United States Patent [19]

Haswell

[11] 4,149,537

[45] Apr. 17, 1979

[54] POSTPARTUM FLUID LOSS RECEPTACLE

[76] Inventor: John N. Haswell, 607 Dubois St., Vincennes, Ind. 47591

[21] Appl. No.: 852,868

[22] Filed: Nov. 18, 1977

Related U.S. Application Data

[62] Division of Ser. No. 657,161, Feb. 11, 1976, Pat. No. 4,076,017.

[51] Int. Cl.² .............................................. A61B 19/00
[52] U.S. Cl. ..................................... 128/292; 128/2 F
[58] Field of Search ................... 128/2 F, 132 D, 286, 128/284, 275, 292

[56] References Cited

U.S. PATENT DOCUMENTS

| | | | |
|---|---|---|---|
| 1,597,556 | 8/1926 | Townsend | 128/292 |
| 3,494,356 | 2/1970 | Melges | 128/292 |
| 3,646,938 | 3/1972 | Haswell | 128/292 |

*Primary Examiner*—William E. Kamm
*Attorney, Agent, or Firm*—Woodard, Weikart, Emhardt & Naughton

[57] ABSTRACT

A postpartum fluid loss receptacle is disclosed herein comprising a sheet which is positioned beneath the patient. The receptacle includes a pocket formed by folding an edge of a non-absorbent sheet upon itself and sealing it together. The pocket collects the fluid and includes graduations to permit measurement of the amount of the fluid.

2 Claims, 3 Drawing Figures

U.S. Patent  Apr. 17, 1979  4,149,537
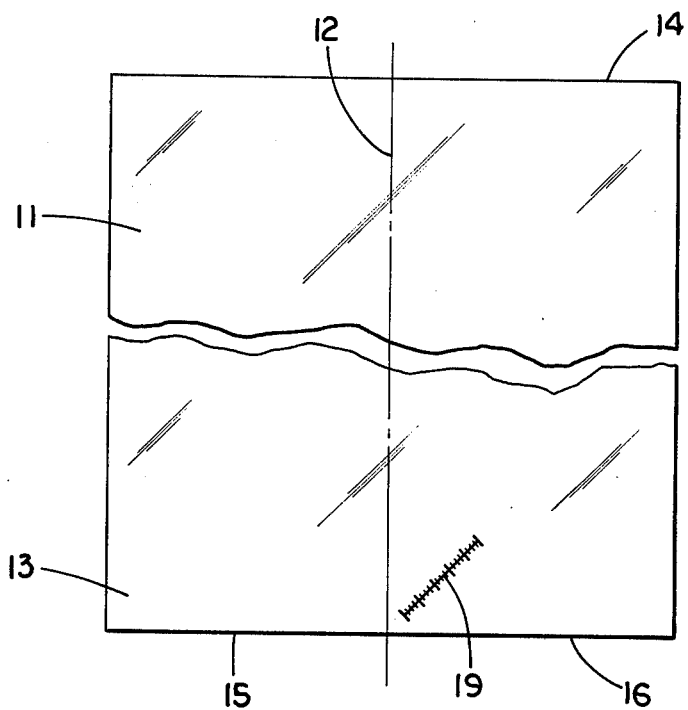
Fig.1
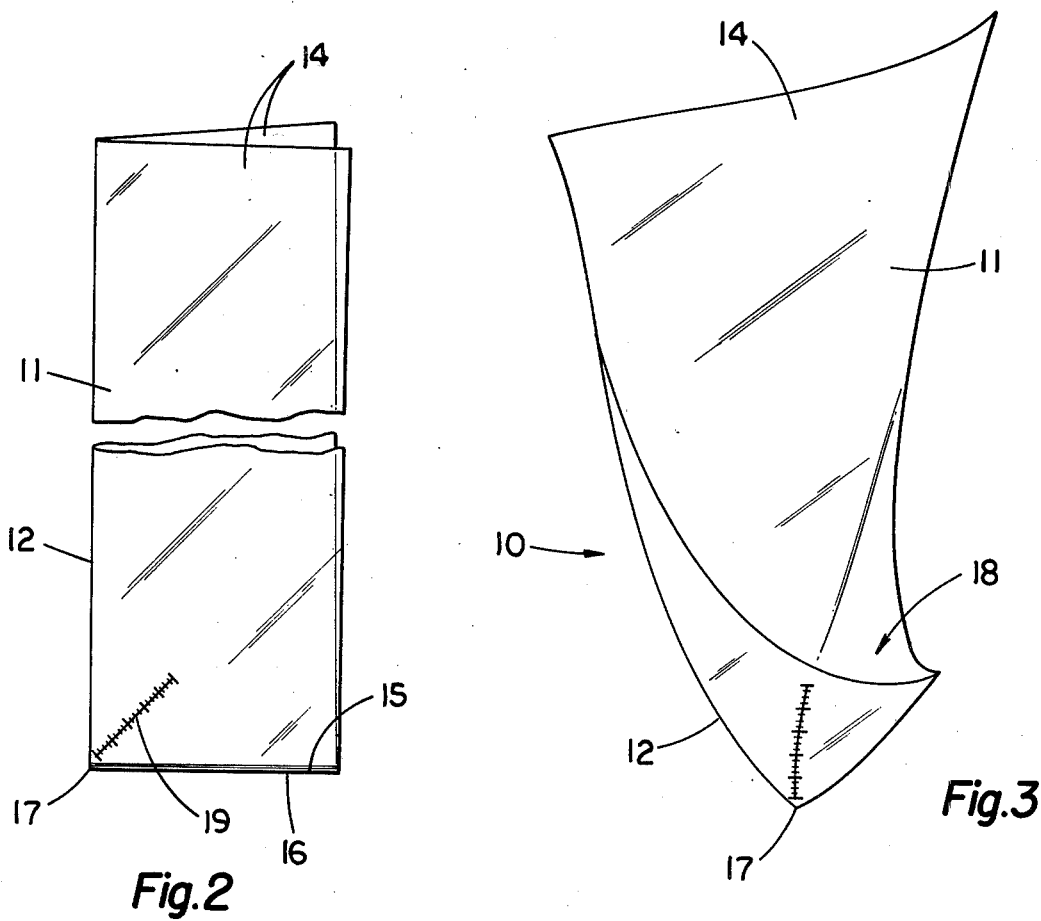
Fig.2
Fig.3

POSTPARTUM FLUID LOSS RECEPTACLE

This is a division of application Ser. No. 657,161, filed Feb. 11, 1976, and issued on Feb. 28, 1978 as U.S. Pat. No. 4,076,017.

BACKGROUND OF THE INVENTION

1. Field of the Invention

This invention relates to receptacles for collecting and measuring the amount of postpartum fluid loss.

2. Description of the Prior Art

Surgical drapes are customarily used in operating rooms. The drapes protect the surgically prepared areas of the skin from contamination. Unprepared portions of the skin and of the room are also isolated by the drapes from the prepared areas, thereby reducing the potential for contamination due to these sources.

Surgical drapes are also employed in a delivery room when a woman gives birth to a child. During delivery, the woman will lose a significant amount of amniotic fluid and blood. It is desirable that these fluids be collected to protect the delivery table and surrounding areas from being unduly soiled. Additionally, collection of these fluids permits the physician to determine the proper treatment of the mother, and to evaluate the mother's speed of recovery. Present surgical drapes do not permit the postpartum fluids to be easily and totally collected and readily measured.

A method and device for collecting and measuring postpartum blood loss is disclosed in my U.S. Pat. No. 3,646,938, issued on Mar. 7, 1972. The device therein disclosed comprises a substantially flat, pliable sheet. The sheet is placed beneath the buttocks of the patient, and the blood lost is collected thereon. When held pendantly, the sheet causes the blood to pool and graduations on the sheet permit measurement of the blood collected to be made. The device and method of this previous patent do permit collection and measurement of postpartum blood loss. One aspect of the present invention, however, is the provision of an improved device of the type described in my previous patent, the improvement facilitating increased accuracy in the measurement of the amount of blood collected.

SUMMARY OF THE INVENTION

A postpartum fluid loss receptacle is disclosed herein which comprises a first elongated sheet of flexible material that is essentially nonabsorbent to body fluids, the first sheet having a first end portion forming a first pocket and a second end portion, the first end portion of the first sheet being folded and defining a first edge and a second edge, the edges having a common point, the first edge being sealingly attached to the second edge continuously along a line extending from the common point.

It is an object of the present invention to provide a postpartum fluid loss receptacle which is easily used and fully collects the lost fluids.

An additional object of this invention is to provide a postpartum fluid loss receptacle which is easily constructed and is inexpensive.

Another object of the present invention is to provide a postpartum fluid loss receptacle which protects against contamination and prevents the delivery table and room from becoming soiled.

A further object of the present invention is to provide a postpartum fluid loss receptacle which permits the amniotic fluid and the blood to be collected.

It is yet another object of this invention to provide a postpartum fluid loss receptacle which enables the volume of fluids collected to be readily determined.

Further objects and advantages of the present invention will become apparent from the description and figures which follow.

BRIEF DESCRIPTION OF THE DRAWINGS

FIG. 1 is a top view of material utilized in constructing an embodiment of the receptacle of the present invention.

FIG. 2 is a top view of the material of FIG. 1 with one side folded against the other side.

FIG. 3 is a perspective view of an embodiment of the receptacle of the present invention.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The postpartum fluid loss receptacle of the present invention provides a simple and efficient means for collecting and measuring the amount of fluid lost by a woman in conjunction with giving birth to a child. The material from which the receptacle is constructed must therefore be suitable for surgical use. Primarily, the material should be aseptic and should be easily manipulated by the persons attending the woman during and after childbirth.

A second requirement of the material comprising the present receptacle is that it have sufficient flexibility and strength. The material should be flexible or pliable to permit the receptacle to be folded for transportation and storage. At the same time, the materials should be strong enough to support the weight of the fluids which will be collected therein. The present receptacle is designed primarily to collect the amniotic fluid and the blood which is lost during and subsequent to childbirth.

Referring in particular to FIGS. 1-3, there is shown one embodiment of the receptacle according to the present invention. The receptacle 10 comprises a flexible sheet 11 which includes a first end portion 13 and a second end portion 14. The material is preferably a transparent plastic, and should be essentially nonabsorbent to body fluids. The sheet 11 is folded along the longitudinal center line 12, the folded first end portion defining a first edge 15 and a second edge 16. The first edge 15 is sealingly attached to the second edge 16 along a line extending from the common point 17. The seam 26 may have any shape but is most conveniently a straight line. The second end portion is then opened up to be flat, and the first end portion forms a pocket 18.

Graduations 19 are included at the first end portion along the side of pocket 18 to indicate the volume of material contained within the pocket 18. The graduations may correspond to any measuring system, but preferably indicate the volume in cubic centimeters or milliliters. The graduations should read at least as high as 500 cubic centimeters, and indications at every 50 cc are appropriate.

The positioning of the receptacle 10 for its intended use has the second end portion 14 positioned upon the delivery table, and the first end portion 13 is suspended over the side of the table. The patient is positioned to have her buttocks upon the second end portion 14, and the weight of the patient acts to hold the second end portion 14 upon the table. A rigid receptacle is positioned on the floor of the delivery room to support the pocket 18. The "kick bucket" which is generally found in a delivery room may be used for this purpose.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention and the scope of the claims are desired to be protected.

What is claimed is:

1. A postpartum fluid loss receptacle which comprises a first sheet of flexible material that is essentially nonabsorbent to body fluids, said first sheet having a first end portion forming a first pocket and a second end portion, the first end portion of said first sheet having an end edge, the first end portion being folded upon itself, the end edge of the first end portion comprising a first edge and a second edge having a common point at the fold, the first edge being adjacent and sealingly attached to the second edge continuously along a line extending from the common point to form a pocket within which fluids are retainable, said first sheet including side edges extending from the end edge, the side edges being separate throughout their length, only the first and second edges being sealed together.

2. The receptacle of claim 1 in which the first end portion further includes graduations to indicate the volume of material contained within the first pocket.

* * * * *